United States Patent [19]

Engelbrecht et al.

[11] Patent Number: 4,806,381

[45] Date of Patent: Feb. 21, 1989

[54] POLYMERIZABLE COMPOUNDS CONTAINING ACID AND ACID DERIVATIVES, MIXTURES CONTAINING THE SAME, AND USE THEREOF

[75] Inventors: Jürgen Engelbrecht, Hamburg; Helmut von Wallis, Henstedt-Ulzburg; Michael Günther, Hamburg, all of Fed. Rep. of Germany

[73] Assignee: Ernst Muhlbauer KG, Hamburg, Fed. Rep. of Germany

[21] Appl. No.: 916,588

[22] Filed: Oct. 8, 1986

[30] Foreign Application Priority Data

Oct. 9, 1985 [DE] Fed. Rep. of Germany ....... 3536077

[51] Int. Cl.$^4$ .................... A01N 1/02; B05D 3/02; A61K 6/08; A61K 5/01
[52] U.S. Cl. .......................................... 427/2; 106/35; 427/385.5; 433/228.1; 523/116; 525/285; 525/287; 525/291; 525/301
[58] Field of Search ................... 106/35; 427/2, 385.5; 525/285, 287, 291, 301; 523/116; 433/228.1

[56] References Cited

U.S. PATENT DOCUMENTS

| | | | |
|---|---|---|---|
| 4,499,251 | 2/1985 | Omura et al. | 106/35 X |
| 4,515,910 | 5/1985 | Rawls et al. | 106/35 X |
| 4,535,102 | 8/1985 | Kusumoto et al. | 525/285 X |
| 4,585,833 | 4/1986 | Domeier | 525/285 X |
| 4,599,373 | 7/1986 | Jones | 523/116 |

FOREIGN PATENT DOCUMENTS 0130806 7/1984 Japan ..................................... 106/35

*Primary Examiner*—Michael Lusignan
*Attorney, Agent, or Firm*—Sprung Horn Kramer & Woods

[57] ABSTRACT

Oligomeric or prepolymeric organic compounds that contain both polymerizable unsaturated groups and acid radicals, their salts, or their reactive-derivative radicals. The compounds exhibit outstanding adhesion properties, especially to biological substrates, and are appropriate for application as bonding agents, adhesive filling materials, or adhesive cements in the fields of dentistry and medicine.

32 Claims, No Drawings

POLYMERIZABLE COMPOUNDS CONTAINING ACID AND ACID DERIVATIVES, MIXTURES CONTAINING THE SAME, AND USE THEREOF

The invention concerns polymerizable compounds containing acid groups or acid-group derivatives, mixtures containing the same, and the use thereof.

Compounds of this type adhere to various substrates, especially biological substrates. The compounds can be employed or added for general purposes, but especially in the dental and medical fields as constituents of polymerizable bonding agents, adhesive fillers, and adhesive cement and for similar mixtures.

Polymerizable mixtures based on monomeric compounds provided with one or more unsaturated groups constitute a basis for a number of plastics, with compounds having methacrylate groups being especially important in the dental and medical fields. Mixtures of this type constitute for instance the basis of acrylic-based filling and sealing materials.

These polymerizable mixtures cannot, however, generally establish any chemical bond with other materials, especially biological substrates, even when the substrates themselves contain sufficient unpolymerized polymerizable groups.

A more secure bond can accordingly be attained only through the use of highly retentive surfaces, by means that is of strictly mechanical bonding—by etching the surface of biological or inorganic materials. This drawback can, however, be eliminated by using bonding agents, substrates that is that can react chemically with biological or inorganic material as well as containing a polymerizable group.

A series of such bonding agents is known—the organosilanes with vinyl or methacryl groups for example. They are however, restricted in their adhesiveness to silicon dioxide, to glasses and ceramics that contain silicon dioxides, and to metal oxides or non-precious metals that form them. They exhibit no adhesion to biological substrates, especially dental and osseous substrates, but tend rather to have a separating action.

A series of polymerizable bonding agents with other adhesive groups, like 2-N-allylamino-4,6-dichloro-1,3,5-triazine (U.S. Pat. No. 4,203,220), combinations of hydroxymethacrylic esters with dialdehydes (Eur. Pat. No. 0 141 324), or epoxymethacrylates, have been discovered for substrates of this type. They react with the collagen or collagen-like constituents of the substrates.

There are also a number of polymerizable compounds that react with the apatite compounds in the dental and osseous tissues. These bonding-promotion compounds include acid groups or reactive acid-group derivative. Examples of such polymerizable compounds are unsaturated organic esters of phosphoric or phosphonic acids (German AS No. 2 711 234 & German OS No. 3 150 285), unsaturated organic esters of monofluorophosphoric acid (U.S. Pat. No. 3,997,504), unsaturated organic esters of phosphoric acids that contain either chlorine or bromine bonded directly to the phosphorus (Eur. Pat. No. 0 058 483), and unsaturated organic esters of phosphoric acid in the form of pyrophosphates (anhydrides) (German OS No. 3 048 410).

Also known are polymerizable carboxylic acids and reactive derivatives of carboxylic acids that exhibit satisfactory adhesion to the dental tissue. These include 4-methacryloyloxyethyltrimellitic acid and its anhydride (M. Takeyama et al., I. Jap. Soc. f. Dent. App. a. Mat. 19, 170 [1978]) and bis-2-methacryloylethyl pyromellitate. Their application, however, is very limited. Solutions in acetone or methyl methacrylate are employed.

In dimethacrylate systems like mixtures that include bis-GMA, separation and other problems like spontaneous polymerization or failure to cure occur, and the admixtures must remain less than 5% (V. P. Thompson, IADR Symposium 1985, Publ. 1103).

The aforesaid polymerizable compounds do make it possible in many cases to obtain more or less powerful adhesion on the part of acrylic-based filling and sealing materials to the dental and osseous tissues. Success, however, also depends extensively on how thick a coating of the bonding agent is applied, on how many adhesive groups enter into reaction with the biological substrate, and on how many polymerizable groups enter into reaction with the copolymerizing material.

The object of the invention is to discover compounds that contain several polymerizable groups and several adhesive groups bonded to chemically very stable molecular backbones. This object is attained in accordance with the invention by means of oligomeric or prepolymeric organic compounds that contain several polymerizable unsaturated groups as well as several acid radicals, their salts, or their reactive derivative radicals.

It has been discovered that such compounds can be obtained by preparing oligomer or polymeric backbones in the form of homo- or co-oligomers or homo- or co-polymers that contain the desired acid groups or acid-derivative groups and/or functional groups that the desired acid groups or acid-derivative groups can be grafted to.

The compounds in accordance with the invention contain in a practical way three or more polymerizable unsaturated groups and three or more acid radicals, their salts or their reactive derivatives, whereby, depending on the substrate that the compounds are to adhere to and on the polymerizable system that they are contained in or that they are to polymerize with, a choice can be made as to whether there are to be more acid groups or more polymerizable groups or whether the same number of groups is to be present.

Appropriate polymerizable unsaturated groups are all alkenyl, alkenoxy, cycloalkenyl, aralkenyl, and alkenaryl radicals, in practical terms however, acryl, methacryl, vinyl, and styryl radicals, and of these in especially practical terms the acryl and methacryl radicals that constitute the polymerizable groups of many monomers in dental materials.

Especially appropriate acid groups in the compounds in accordance with the invention are in principle all those that exhibit adhesiveness to oxidic, mineral, ceramic, vitreous, metallic, or biological substrates. It is practical however, to employ carboxylic-acid radicals, the radicals

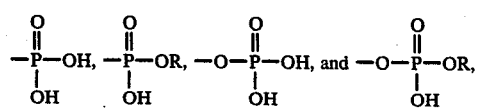

of phosphoric acids wherein R is alkyl, aryl, or vinyl for example, the radicals $-SO_2H$, $SO_3H$, or $-O-SO_3H$ of sulfuric acids, and the radicals

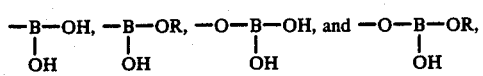

of boric acids wherein R is alkyl, aryl, or vinyl.

Cationic acid radicals such as $-NR_2H^+$ or $-PR_2H^+$ (wherein R is H or alkyl) are also appropriate.

It is, however, especially practical to graft the carboxylate, phosphate, sulfonate, and borate radicals or their reactive derivatives to the oligomeric or polymeric backbone. With derivatives of multibasic acids in the presence of one readily hydroylzing group will be sufficient, and the others can be stable-substituted.

The reactive acid derivatives of the compounds in accordance with the invention can be substituted with acid halides, with acid anhydrides, and with acid amides, nitriles, and esters that readily hydrolyze into acid, like silyl or tert.-butyl for instance.

The oligomeric or polymeric backbones can be linear, branched, or cyclic.

They can be polymers of ethylenically unsaturated monomers or they can be oligomeric or polymeric compounds, like polyesters, polyamides, polyethers, polyphosphazenes, polysaccharides, etc. for instance, if their backbone is sufficiently hydrolysis-stable, if they can be supplied with the desired polymerizable groups, and if they include or can be supplied with the desired acid groups.

The desired groups can be grafted if the backbone contains a number of bound functional groups, like alcohols, halogens, acid halides, amines, epoxides, or isocyanates, that allow such a grafting reaction.

This means that the aforesaid backbones can, no matter what components they are constructed out of, be present in the form of polyalcohols, polyhalides, polyacid halides, polyamines, polyepoxides, or polyisocyanates or of mixtures thereof.

Preferred backbones are the polymers of ethylenically unsaturated monomers.

A group of monomers that results in homo-oligomers or homo-polymers is appropriate on the one hand, and, on the other, a group that results in co-oligomers or co-polymers by means of a combination of different monomers. Oligomers or polymers of unsaturated acids employed in the acid-chloride form,

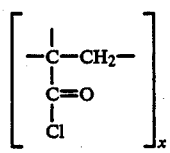

(A)

are the appropriate examples from the homopolymer group. They can be converted to a desired level with hydroxyethyl methacrylate for example in a first step if the free acid group is desired, with the acid-chloride radical being hydrolyzed in a second step. The statistical distribution of the groups is for example

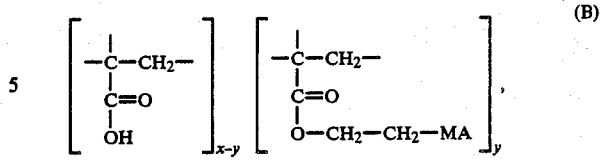

(B)

whereby MA is a methacryl radical

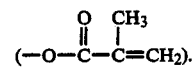

The second stage (hydrolysis) can, however, be replaced by means of alcoholysis with alcohols, such as 1-hydroxyethane-1,1-diphosphonic acid, that contain acid groups to obtain products such as

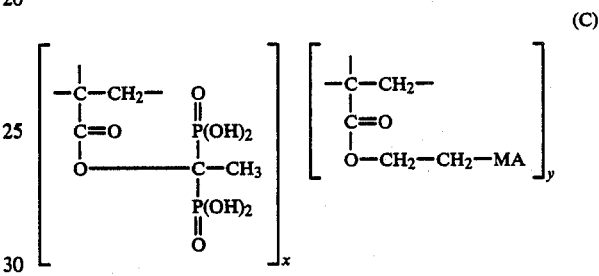

(C)

Another good backbone for compounds in accordance with the invention is provided by homopolymers of unsaturated alcohols:

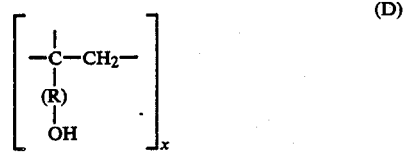

(D)

wherein R is absent or is an inert radical. Some of the hydroxy groups can be provided with polymerizable groups by for example esterification with an unsaturated acid or with an unsaturated acid chloride. Others can be converted into corresponding compounds

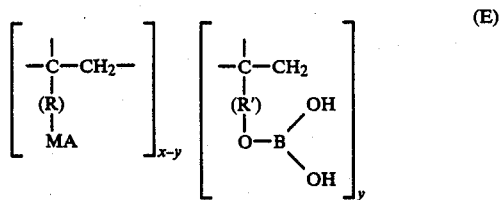

(E)

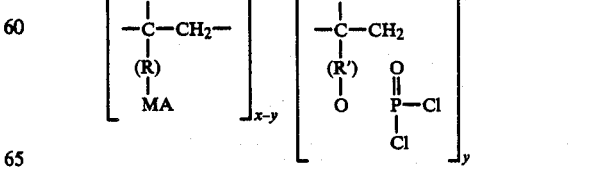

(F)

in accordance with the invention, wherein R and R' are absent or are inert radicals, by means of acids or acid chlorides like boric acid or phosphoryl chloride for example.

Especially preferred are oligomers or polymers of maleic acid anhydride:

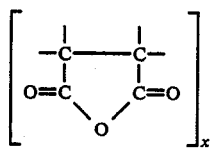

which can be converted with a hydroxyalkylmethacrylate for instance in a ratio of 1:1 into products such as

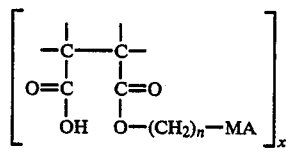

A product with two different adhesive groups in accordance with the invention,

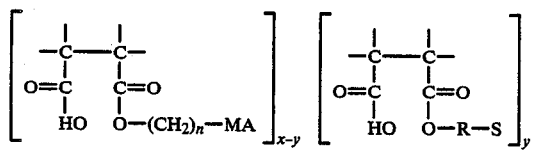

whereby S is the acid radical or acid-derivative radical absolutely in general and R is any radical, can be obtained by adding less hydroxy methacrylate and making up for it with more of the hydroxy-acid derivative.

In another group of preferred fundamental compounds—specifically co-oligomers or co-polymers—vinyl, styrene, or (meth)acryl monomers like vinyl phosphate, vinyl phosphonate, methacrylates of phosphoric acids or phosphonic acids, and styryl compounds with phosphoric, boric, and sulfuric acid groups, like sulfonated styrene for example, that contain acid or an acid derivative can be copolymerized with unsaturated compounds like vinyl chloroacetate or chloromethylated styrene into compounds like for example

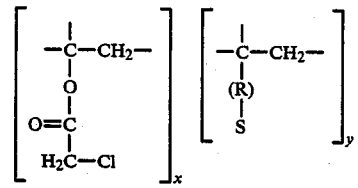

or, for example

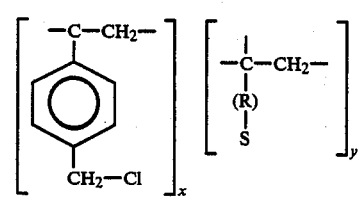

Compounds of this type can then be converted with sodium methacrylate for example into a polymerizable compound

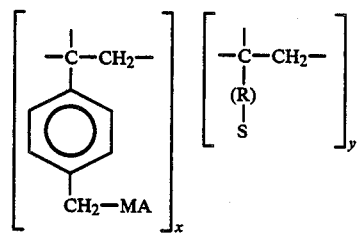

in accordance with the invention.

Copolymers

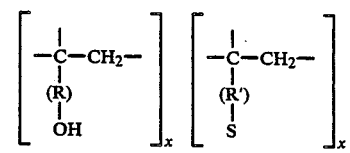

of unsaturated alcohols and unsaturated acids also result subsequent to reaction with compounds like methacrylic-acid chloride in products

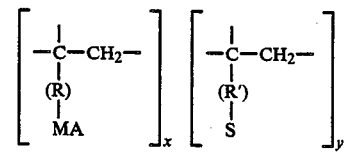

in accordance with the invention.

In constructing the backbone, units that do not have acid groups that are not supplied with a polymerizable group can also be polymerized in. It can on the one hand be practical to do so in order to modify the solubility, as for example by inserting inert methyl methacrylate units

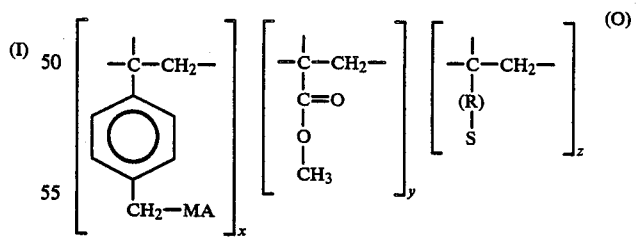

The insertion of additional units with halotriazine, epoxide, isocyanate, or aldehyde groups

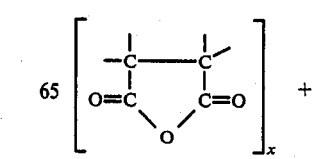

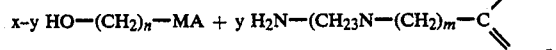

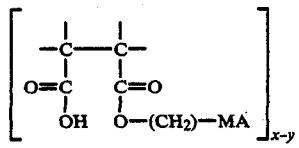

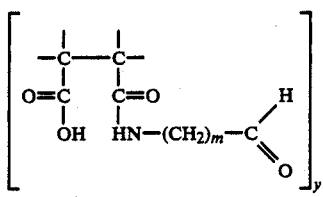

can on the other hand also be useful to induce an additional reaction with the collagen constituent of the dental or osseous tissue.

The insertion of units with groups that can be components of a polymerization-catalyst system can be of advantage. The groups do not absolutely have to be present as groups of that kind during the homo- or co-polymerization of the backbone, but can be grafted on subsequently by means for example of a halogen-, alcohol-, anhydride-, or amine-functional group.

The reaction methods that result in the oligomeric or prepolymeric fundamental compounds can be determined by the choice of solvent, solubilities, concentration, temperatures, and polymerization catalysts and are known to one skilled in the art.

It can be important for the polymerization catalysts to be destroyed by the reaction itself or for any residues to be removed before the polymerizable groups in accordance with the invention are introduced.

It is practical for the oligomeric compounds in accordance with the invention to have a molecular weight of more than 500, and for the prepolymeric compounds to have one of greater than 1500, although preferably no greater than 100,000, and particularly preferably no greater than 20,000.

The compounds in accordance with the invention can be employed by themselves, but preferably in a mixture with other polymerizable compounds.

Thus, the mixtures can also contain polymerizable unsaturated monomers, oligomers or polymers that do not contain any acid groups, salts thereof, or reactive derivative groups thereof. Particularly appropriate are monomers that are constituents of conventional polymerizable composites and of polymerizable dental-resin mixtures such as for example bis-GMA or triethyleneglycol dimethacrylate.

The mixtures can also contain admixtures of known monomeric polymerizable unsaturated compounds that contain acid groups, their salts, or their reactive derivative groups. Polymerizable compounds with groups that exhibit especially satisfactory adhesion to the collagen in the dentin and that are specified in the aforementioned publications are also a preferred additive.

The mixtures can if necessary also contain other compounds that, although they contain acid groups, their salts, or their reactive derivative groups, do not contain polymerizable groups. Preferred in this case are multibasic acids such as tartaric, citric, mellitic, polycarboxylic, polyphosphoric, polyphosphonic, or polysulfonic acids along with chelating agents such as ethylenediamine-tetraacetic acid, and especially their salts.

It can also be an advantage to add anhydrides of multibasic acids such as pyromellitic-acid anhydride or 1,2,3,4-cyclopentane-tetracarboxylic acid, especially if an alcoholic compound is added to a bicomponent mixture. It is also helpful to add a highly volatile solvent in order to keep the coating of the mixture on the article that it is to adhere to very thin. Such an additive can also be effective when several constituents have to be stored separately or when they do not dissolve readily enough in the compounds in accordance with the invention or in the mixtures that contain them.

Appropriate polymerization catalysts in principle are all those systems that can trigger the radical polymerization of olefinic compounds. Whether the catalyst reaction is initiated by heating, by the introduction of an activator, or by photoirradiation is not essential. What is important, however, is for the catalyst system to dissolve satisfactorily in the mixture and essentially not be blocked or disintegrated by polymerizable compounds that contain acid groups or acid-derivative groups.

Preferred for light-curing (photocuring) mixtures are curing systems consisting of $\alpha$-diketones and tertiary amines such as those specified in French Pat. No. 2 156 760 for instance or of combinations of sulfinic-acid salts and of xanthones or thioxanthones such as those specified in European Pat. No. 0 132 318 for instance.

Especially appropriate for bicomponent mixtures are combinations of one constituent that contains organic peroxides and of another constituent that contains a tertiary amine and a compound that exhibits sulfur in oxidation number +2 or +4.

The constituent that does not contain the peroxide can preferably also contain bivalent metal ions, especially that of calcium, particularly when tertiary butyl permaleate is employed as the peroxide.

Especially preferred are benzoyl peroxide for the organic peroxide and sodium para-toluene sulfinate as the sulfur compound.

An especially practical mixture results when alcohols that contain one or more polymerizable olefinic unsaturated groups are added to the constituent that contains the sodium sulfonate to ensure adequate solubility of that salt.

Appropriate for this purpose are for example hydroxyalkyl methacrylates such as hydroxyethyl methacrylate or vinyl compounds, such as allyl alcohol, that contain hydroxy groups, and especially dimethacrylate compounds, such as bisphenol-A-glycidyl methacrylate or glycerol dimethacrylate, that contain hydroxyl groups, and divinyl compounds, such as glycerindiallyl ether, that contain hydroxyl groups.

It is generally necessary to add 10 to 20% of these polymerizable monomers that contain hydroxyl groups. Slight amounts of salts of heavy metals such as iron, copper, manganese, cobalt, tin, chromium, nickel, and zinc can likewise be added to promote adhesion to the dental tissue for example.

Curative constituents such as cortisone or corticoids, neatsfoot oil, etc. can also be added if indicated for strictly medicinal purposes. Compounds, such as sodium fluorophosphate or aminofluorides, that donate fluoride can also be added for similar reasons.

The mixtures that contain the compounds in accordance with the invention can also be treated with organic or inorganic fillers that have been surface-treated if necessary, whereby the inorganic filler can belong to the group that is conventional for composites and that consists of quartz powders, microfine silicic acid, aluminum oxide, barium glasses, and other (inert) mineral substances, silanized if possible, as well as to a group that is practical for the compounds in accordance with the invention and that consists of finely divided fillers such as powdered metal oxides, metal hydroxides, reactive glasses and ceramics, zeolites, non-precious metals, apatite, etc. that can enter into a bond with the acid groups, salts, or acid-derivative groups in the polymerizable compounds in accordance with the invention.

The compounds in accordance with the invention are new and their properties can easily be modified by varying the ratios of polymerizable groups to adhesive acid groups or to acid-derivative groups as well as by selecting the size of the molecules. Many compounds with outstanding adhesive properties can be produced. Alone or in mixtures with other polymerizable compounds, they can have various fillers added to them and will, once they have cured, be mechanically very strong materials that adhere to a wide range of substrates. Even when restricted to 1 to 10% of the compounds in accordance with the invention, the polymerizable mixtures will, whether filled or unfilled, exhibit, subsequent to polymerization, definite adhesiveness or improved adhesion to various oxidic, mineral, ceramic, vitreous, metallic, or biological substrates as well as a very secure bond with composites that are grafted on just before or just after.

Especially in relation to adhesion to the dental and osseous tissues, the potential for reliable adhesive mixtures and for compositions containing filling and sealing materials that will last longer as bonding agents to the same and as cements between these substrates will be improved.

The fillers can be worked into polymerizable mixtures better and will result in greater strength due to the compounds in accordance with the invention.

Even cured products can be preferably employed. They will also exhibit surfaces that are still reactive although no longer polymerizable, and hence capable of chemical coupling.

The same is true of cured films based on pigments or fillers. These are bonded to and around the filler, making the filler itself inert, but can still set within cement systems for example due to the acid groups that have oxidic constituents.

The invention will now be illustrated with reference to the following examples. Unless otherwise specified the portions are in percent by weight.

EXAMPLE 1

Preparation of a prepolymeric polymethacrylated polyacrylic acid 86 g of anhydrous polyacrylic acid with a molecular weight of approximately 5000 was treated with 130 g of freshly distilled thionyl chloride, 300 ml of tetrahydrofuran, and 200 ml of dioxan and refluxed until no more gas evolved. The excess thionyl chloride was then completely distilled off and treated with another 100 ml of dioxan. 120 g of triethylamine was added and the batch was slowly treated with 135 g of hydroxyethyl methacrylate while being chilled with ice. The triethylamine and tetrahydrofuran were distilled off and the remaining dioxan solution hydrolyzed by adding 10 ml of water. All the volatile components were drawn off, the residue was extracted with ethyl alcohol, and the alcoholic solution evaporated and washed with hexane. The yield was 42 g of a viscous reddish oil.

The IR spectrum exhibited olefinic double bonds ($1640 \text{ cm}^{-1}$) and carboxylic-acid radicals. The product reacts definitely acidic (pH 3.5) and is easily gelled when benzoyl peroxide and activator are added.

EXAMPLE 2

Preparation of a polymerizable adhesion-promoting mixture

A resin was prepared from
50 parts bisphenol-A-glycidyl dimethacrylate (bis-GMA)
50 parts triethyleneglycol dimethacrylate (TEDMA)
5 parts of the product from Example 1
1 part benzoyl peroxide.
and a solution of
96 parts ethyl alcohol
3 parts sodium benzene sulfonate
1 part N,N-bis-hydroxyethyl-p-toluidine
was prepared.

Bovine teeth were prepared as specified in European Pat. No. 0 058 483. 2 drops of the resin and of the solution were mixed together intensively (20 sec.), brushed onto the unetched surface of the dentin, and dried. The commercially available composite, Composite Merz, was allowed to cure thereon in a $5 \times 5$ mm mold.

The samples were allowed to stand for 24 hours and the filler was withdrawn from the teeth in a tensile-strength testing apparatus. The average measured value at which the samples were torn off was $3.57 \text{ N/mm}^2$.

EXAMPLE 3

Control for Example 2

A resin was prepared from
50 parts bis-GMA
50 parts TEDMA
1 part benzoyl peroxide
and mixed with the same solution employed in Example 2. The mixture was brushed onto similarly prepared teeth, dried, and allowed to cure with Composite Merz.

Subsequent to 24 hours a tensile strength of of only $0.80 \text{ N/mm}^2$ was measured.

EXAMPLE 4

Preparation of a polymethacrylated oligomaleic acid 260 g of maleic acid anhydride were refluxed with 2000 ml of toluene and 40 g of benzoyl peroxide for 6 years. A brownish-orange precipitate occurred. Upon termination of the reaction the remaining toluene solution was decanted and the residue washed with hexane. The yield was 200 g, which was treated with an equal volume of tetrahydrofuran.

A mean molecular weight of 439 was determined, corresponding to an approximate oligomerization degree of 4 maleic acid anhydride units. The IR spectrum exhibited the C=O band of anhydride groups ($1790 \text{ cm}^1$) but no acid-OH or double bonds.

100 g of the solution of oligomaleic acid anhydride in tetrahydrofuran were treated with 10 g of powdered zinc, stirred, and filtered again. The solution was definitely light in color.

60 g of hydroxyethyl methacrylate and catalytic volumes of orthophosphoric acid were added and the batch was allowed to stand for 2 weeks. The mixture was definitely viscous. Drawing off the volatile constituents in the vacuum and washing the batch in hexane resulted in a viscous oil that dissolved very well in acetone, and in TEDMA and bis-GMA as well.

The anhydride C=O band in the IR spectrum was almost invisible, although an acid-OH band and a double-bond band were definitely evident.

EXAMPLE 5

An adhesive light-curing mixture (adhesive composite) was prepared from
50 parts bis-GMA
50 parts TEDMA
1 part camphor quinone
1 part dimethylaminoethyl methacrylic ester
1 part butyl dimethyaniline
50 parts of the product of Example 4
150 parts finely divided silanized silicon dioxide.

The mixture was thin and pasty, and polymerized within 40 seconds into a very hard and difficult-to-break material when irradiated with a halide lamp. Without the preliminary admixture of adhesion promoters it exhibited mean dentin-adhesion values of 2.5 N/mm$^2$, whereas conventional composites were measured at approximately 0.2-0.6 N/mm$^2$.

EXAMPLE 6

Preparation of a polymethacrylated polycarboxylpolyphosphonic acid

Powdered zinc was stirred into 100 g of the solution of oligomaleic acid anhydride in tetrahydrofuran from Example 4, and the batch was treated with 30 g of hydroxyethyl methacrylate.

The mixture was allowed to react for 2 weeks at room temperature. 40 g of hydroxyethane-1,1-diphosphonic acid was dissolved therein and the batch was allowed to stand for 2 more weeks.

Evaporating the tetrahydrofuran resulted in a rather viscous liquid, which was washed with hexane. The IR spectrum exhibited C=C bands at 1640 cm$^{-1}$ and P(O)OH bands at 1200 cm$^{-1}$. The substance reacts like an acid and gels when activator and peroxide are added.

EXAMPLE 7

A curing adhesion-promoting resin prepared from
50 parts bis-GMA
50 parts TEDMA
10 parts of the product from Example 6
1 part benzoyl peroxide
was mixed with the solution from Example 1 and applied to dentin as described in Example 1.

The same procedure was followed with the dentin adhesive Scotch Bond (3M).

Both substances were cured together with Composite Merz, and their tensile strengths measured 24 hours later.

Whereas the strength of the Scotch Bond was measured at only 2.7 N/mm$^2$, the mixture that included the component in accordance with the invention exhibited a value of 3.8 N/mm$^2$.

EXAMPLE 8

Preparation of a prepolymeric polymethacrylated polychlorophosphate 42 p of hydroxyethyl methacrylate and 8 g of lauroyl peroxide were dissolved in 400 ml of toluene and allowed to stand for 1 hour at 65° C. The resulting powder was filtered out, washed with hexane, and dried.

The yield was 40 g of polyhydroxyethyl methacrylate (poly-HEMA). The molecular weight was 5700, approximately 44 monomer units. The IR spectrum was identical to that of the high-molecular poly-HEMA product manufactured by the firm of Aldrich.

8 g of methacrylic-acid chloride and 8 g of triethylamine were stirred with 13 g of the laboratory poly-HEMA over a period of 3 days. The precipitate was washed with water and dried.

The yield was 15 g of partly methacrylated poly-HEMA.

3.3 g of this powder were added along with 1.5 g of phosphoryl chloride to 50 ml of tetrahydrofuran, and the batch was stirred over a period of 4 days at room temperature. The precipitate was filtered out and washed with hexane, resulting in 3.8 g of a white powder. Its IR spectrum can be satisfactorily equated with that of a polymethacrylated product with —O—P-(O)Cl$_2$ groups. The powder hardly continues to exhibit any C—OH bands but still has the C=O (1730 cm$^{-1}$) and C=C (1640 cm$^{-1}$) bands as well as revealing new bands in the P—O—alkyl range (1030 cm$^{-1}$).

EXAMPLE 9

Preparation of a halide-curing dentin-adhesive mixture
55 parts bis-GMA
45 parts TEDMA
5 parts polymethacrylated polychlorophosphate (Ex. 8)
1 part butyl dimethylaniline
1 part camphor quinone
were mixed together. The mixture was applied very thin to bovine dentine (treated as described in Example 2), and cured along with cylindrical samples (4 mm in diameter and 6 mm high) of Composite Merz, Light-curing for 2 minutes under a halide light.

Subsequent to 24 hours in water the samples exhibited a mean bond strength on dentin of 4.5 N/mm$^2$ in the tensile-strength test.

Comparison of a dentin-adhesive mixture with no polymethacrylated polychlorophosphate, specifically
55 parts bis-GMA
45 parts TEDMA
1 part butyl dimethylaniline
1 part camphor quinone
was carried out under the same conditions. The mixture exhibited a mean bond strength of only 0.48 N/mm$^2$.

EXAMPLE 10

Preparation of polymethacrylated polyboric acid 3.3 g of the partly methacrylated poly-HEMA from Example 8 were heated with 3.1 g of boric acid and 4.1 g of phosphoric acid in dioxan at 80° C. until termination of precipitation.

The batch was filtered, the filtrate washed free of phosphate and boric acid with water, and dried, yielding 3.45 g of a tannish polymethacrylated polyboric acid.

The C=C and C=O bands in the IR spectrum are unchanged and new (B—OH) bands appear at 3220 cm$^{-1}$. The boron content turns out to be 2.4% by weight.

EXAMPLE 11

Preparation of a dentin-adhesive bicomponent mixture

Equal parts of an activator resin consisting of
55 parts bis-GMA
45 parts TEDMA
3 parts N,N-bis-hydroxyethyl-p-toluidine
and of a catalyst resin consisting of
55 parts bis-GMA
45 parts TEDMA
3 parts benzoyl peroxide
5 parts polymethacrylated polyboric acid (Ex. 10)
were mixed together. The mixture (I) was applied thin to dentin and cured along with a cylinder of Composite Merz.

A comparison was carried out with a mixture (II) of activator and catalyst resins but without the polymethacrylated polyboric acid.

Subsequent to 24 hours in water there was an extensive difference in adhesion to the dentin, with the samples of mixture I exhibiting a mean tensile strength of 7.82 N/mm$^2$ and those of mixture II one of only 0.54 N/mm$^2$.

EXAMPLE 12

Preparation of a polymethacrylated polysulfonate 5.4 g of hydroxyethyl methacrylate, 10.1 g of potassium methacryloylpropylsulfate, and 1.6 g of lauroyl peroxide were heated in 80 ml of methyl alcohol and 20 ml of toluene at 65° C. until termination of precipitation. The batch was filtered and the filtrate washed with hexane and dried.

The yield was 6.4 g of a water-soluble copolymer with a molecular weight of 7490, corresponding to approximately 20 units for each of the monomers employed.

1.88 g of the copolymer was stirred along with 0.54 g of methacrylic-acid chloride and 0.50 g of triethylamine in 50 ml of tetrahydrofuran for 4 days at room temperature. The precipitate was washed with hexane and dried.

The yield was 1.92 g of a white, water-soluble, powdery polymethacrylic polypotassium sulfonate, continuing to exhibit a C=C band at 1640 cm$^{-1}$. The potassium content was 7.9% and the sulfur content 6.2%.

EXAMPLE 13

Preparation of a light-curing adhesive mixture

A mixture of
55 parts bis-GMA
45 parts TEDMA
1 part butyl dimethylaniline
1 part camphor quinone
5 parts polymethacrylic polypotassium sulfonate (Ex. 12)

is tested on bovine dentin as described with reference to Example 9. The result was a mean bond strength of 5.8 N/mm$^2$.

EXAMPLE 14

Agents for bonding methacrylate-based composites to oxidic, mineral, ceramic, vitreous, and metallic substrates A light-curing mixture of
50 parts bis-GMA
50 parts TEDMA
10 parts polymethacrylated oligomaleic acid (Ex. 4)
1 part butyl dimethylaniline
1 part camphor quinone was applied thin to a polished surface of the following substrates and irradiated under a halide light (450–500 nm) for 2 minutes along with cylinders (4 mm in diameter and 6 mm high) of Composite Merz, Light-curing.

After 24 hours in water at 37° C., tensile-strength tests indicated the following bond strength. Control results from tests of the same mixture without the components in accordance with the invention are indicated in parentheses.

|  | N/mm$^2$ | |
|---|---|---|
| Ionomer cement | 5.2 | (1.2) |
| Silicate cement | 17.8 | (0.9) |
| Glass | 12.1 | (0.3) |
| Porcelain | 19.9 | (0.1) |
| Cobalt-chromium alloy | 9.2 | (0.9) |
| Gold-platinum alloy | 3.6 | (0.2) |

EXAMPLE 15

Preparation of a prepolymeric polymethacrylated polymaleic acid 60 g of maleic acid anhydride and 9 g of lauroyl peroxide were refluxed for 4 days in 150 ml of tetrahydrofuran. The tetrahydrofuran was extracted and the resulting viscous oil washed with hexane.

The polymaleic acid anhydride has a molecular weight of 1850, corresponding to approximately 17 units. The IR spectrum was identical with that of the oligomaleic acid anhydride from Example 4.

9.8 g of the oil were dissolved in 30 ml of THF and stirred with 12 g of hydroxyethyl methacrylate for two weeks. The THF was extracted, leaving a viscous oil of polymethacrylated polymaleic acid with an IR spectrum identical to that of the polymethacrylated oligomaleic acid from Example 4.

EXAMPLE 16

A bonding agent

A mixture of
50 parts bis-GMA
50 parts TEDMA
10 parts polymethacrylated polymaleic acid (Ex. 15)
1 part butyl dimethylaniline
1 part camphor quinone is tested by the same procedure described with reference to Example 9. The mean bond strength is 6.8 N/mm$^2$.

EXAMPLE 17

Preparation of a prepolymeric polymethacrylated polyaldehydopolymaleic acid 9.8 g of polymaleic acid anhydride are dissolved in 30 ml of THF, treated with 6 g of hydroxyethyl methacrylate, and stirred for 2 weeks under an HCl atmosphere until free hydroxyethyl methacrylate can no longer be detected. 7.5 g of aminobutyric-aldehyde diethylacetal and a little triethylamine are added and the batch stirred for 3 more days.

The white precipitate was filtered out, the THF extracted, and the remaining oil washed with hexane, dilute HCl, and water, and dried. The oil (polymethacrylic-polyaldehydopolymaleic acid) reduces an alkaline solution of silver in ammonia. Its IR spectrum exhibited C=C bands and COOH bands but ceased to reveal anhydride bands.

EXAMPLE 18

Bonding agent

A mixture of
50 parts bis-GMA
50 parts TEDMA
10 parts polymethacrylated polyaldehydopolymaleic acid
1 part butyl dimethylaniline
1 part camphor quinone is tested on bovine dentin by the procedure described with reference to Example 9. The mean bond strength is 9.5 N/mm$^2$.

EXAMPLE 19

Bonding agent for fingernail material 5 fingernails at a time are coated with either a thin film of the bonding agent from Example 16 (Group 1) or with a thin film of a mixture that is identical except that the polymethacrylated polymaleic acid is left out (Group 2). The coatings are cured along with an approximately 1-mm thick area of about 2×2 mm of Liquicoat, a thin, light-curing composite manufactured by the firm of Merz.

Although the composite layers in Group 2 drop off in 2 days, 4 samples from Group 1 adhere to the fingernails for 2 more weeks.

It will be understood that the specification and examples are illustrative but not limitative of the present invention and that other embodiments within the spirit and scope of the invention will suggest themselves to those skilled in the art.

What is claimed:

1. An oligomeric or prepolymeric organic compound that contains (a) several polymerizable unsaturated groups and (b) several acid radicals, their salts, or their reactive derivatives bonded to (c) an oligomeric or prepolymeric backbone.

2. A compound according to claim 1, containing at least three polymerizable unsaturated groups and at least three acid radicals, their salts, or their reactive derivatives.

3. A compound according to claim 1, wherein the polymerizable unsaturated groups comprise at least one of acrylic, methacrylic, vinyl and styryl groups.

4. A compound according to claim 1, wherein the polymerizable unsaturated groups comprise at least one of acrylic and methacrylic groups.

5. A compound according to claim 1, wherein the acid radicals are carboxylic acid radicals, the radicals

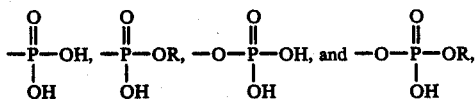

the radicals —SO$_2$H, SO$_3$H, or —O—SO$_3$H or the radicals

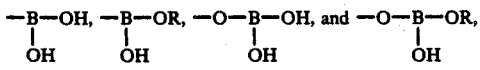

wherein R is alkyl, aryl or vinyl.

6. A compound according to claim 1, wherein (b) is present in the form of an acid halide, acid anhydride, a readily hydrolyzable-into-acid acid amide, acid nitrile, or acid ester.

7. A compound according to claim 1, wherein the oligomeric or prepolymeric backbone (c) is a homo- or co-polymer of ethylenically unsaturated monomers.

8. A compound according to claim 1, wherein the oligomeric or polymeric backbone (c) is a polyester, polyamide, polyether, polysulfone, polyphosphazene, or polysaccharide.

9. A compound according to claim 1, containing aldehyde, epoxide, isocyanate, or halotriazine groups in addition to the acid groups and polymerizable groups.

10. A mixture according to claim 1, wherein the polymerizable unsaturated oligomer of (a) has a molecular weight of at least 500.

11. A mixture according to claim 1, wherein the polymerizable unsaturated prepolymer of (a) has a molecular weight of at least 1,500.

12. A mixture according to claim 1, wherein the polymerizable unsaturated prepolymer of (a) has a molecular weight of maximal 100,000.

13. A mixture according to claim 1, wherein the polymerizable unsaturated prepolymer of (a) has a molecular weight of maximal 20,000.

14. A compound according to claim 1, wherein (a) comprises (meth)acrylic radicals, and (b) comprises a carboxylic group and (c) comprises a poly(meth)acrylic backbone.

15. A compound according to claim 1, wherein (a) comprises (meth)acrylic radicals, and (b) comprises a carboxylic group and (c) comprises an oligomaleic backbone.

16. A compound according to claim 1, wherein (a) comprises (meth)acrylic radicals, and (b) comprises a carboxylic group with (c) comprises a polymaleic backbone.

17. A compound according to claim 1, wherein (a) comprises (meth)acrylic radicals, and (b) comprises carboxylic group and phosphoric groups, and (c) comprises a polymaleic backbone.

18. A compound according to claim 1, wherein (a) comprises (meth)acrylic radicals, and (b) comprises a halophosphoric acid group, and (c) comprises a poly(meth)acrylic backbone.

19. A compound according to claim 1, wherein (a) comprises (meth)acrylic radicals, and (b) comprises a sulfonic acid group, and (c) comprises a poly(meth)acrylic backbone.

20. A compound according to claim 1, wherein (a) comprises (meth)acrylic radicals, and (b) comprises a boric acid group, and (c) comprises a poly(meth)acrylic backbone.

21. A compound according to claim 1, wherein (a) comprises (meth)acrylic radicals, and (b) comprises a carboxylic group, and (c) comprises a polymaleic backbone, and said polymaleic backbone containing aldehydo groups.

22. A polymerizable mixture comprising at least one compound according to claim 1.

23. A polymerizable mixture according to claim 22, further containing one or more polymerizable unsaturated compounds.

24. A polymerizable mixture according to claim 22, further containing compounds with aldehyde, epoxide, isocyanate, or halotriazine groups.

25. A polymerizable mixture according to claim 22, further containing compounds with acid radicals, their salts or their reactive derivatives.

26. A polymerizable mixture according to claim 18, further containing at least one of a solvent, a polymerization catalyst, and a surface-treated or untreated inorganic or organic filler.

27. A method for repairing, filling, veneering or lining oxidic, mineral, vitreous, ceramic, metallic, or biological substrates, applying to said substrates a mixture of claim 22, and causing that mixture to harden.

28. A method for adhering (a) oxidic, mineral, vitreous, ceramic, metallic, or biological substrates to (b) oxidic, vitreous, ceramic, metallic, biological, or acrylic substrates comprising the steps of
(c) applying to said substrates (a) a mixture according to claim 22;
(d) bringing said substrates (b) in good contact with said mixture on said substrates (a) and
(e) causing that composition to harden.

29. A method according to claim 27, wherein said biological substrate is hard dental tissue or bone.

30. A method for coating reactive filler particles, pigments or fibers with a thin film of uncured mixtures according to claim 22, before compounding said filler particles, pigments or fibers with a polymerizable binder resin to create a better bond between said reactive filler particles, pigments or fibers to said polymerizable binder resin.

31. A method for coating reactive filler particles, pigments or fibers with a thin film of cured mixtures according to claim 22, to alter the surface of said reactive filler particles, pigments or fibers to another one.

32. A method for producing a shaped object, moulding a mixture according to claim 22, and causing said mixture to harden.

* * * * *

UNITED STATES PATENT AND TRADEMARK OFFICE
CERTIFICATE OF CORRECTION

PATENT NO. : 4,806,381

DATED : Feb. 21, 1989

INVENTOR(S) : Engelbrecht et al.

It is certified that error appears in the above-identified patent and that said Letters Patent is hereby corrected as shown below:

Col. 3, line 14        Delete "in" after "acids"
Col. 7, line 3         Delete "($CH_2$$_3$N-"

Signed and Sealed this

Eighth Day of May, 1990

Attest:

HARRY F. MANBECK, JR.

*Attesting Officer*        *Commissioner of Patents and Trademarks*